United States Patent [19]

Drake

[11] 4,010,073
[45] Mar. 1, 1977

[54] FREE-FLOWING ENZYME COMPOSITION
[75] Inventor: Billy B. Drake, Philadelphia, Pa.
[73] Assignee: Rohm and Haas Company, Philadelphia, Pa.
[22] Filed: June 25, 1975
[21] Appl. No.: 590,238
[52] U.S. Cl. .............................. 195/64; 195/66 R; 195/68; 426/64; 426/661
[51] Int. Cl.$^2$ ......................................... C12K 1/00
[58] Field of Search ............. 195/63, 64, 66 R, 68, 195/31 R; 426/661, 64

[56] References Cited
UNITED STATES PATENTS

| | | | |
|---|---|---|---|
| 2,979,440 | 4/1961 | Smythe | 195/64 |
| 3,181,998 | 5/1965 | Kanig | 195/63 |
| 3,661,786 | 5/1972 | Desforges | 195/63 |

OTHER PUBLICATIONS

Methods in Enzymology, Colowick and Kaplan Editors, vol. I, (1955), pp. 52–56.
Handbook of Food Additives, Ed. Thomas Furia, The Chemical Rubber Co., (1968), pp. 712, 742.

*Primary Examiner*—A. Louis Monacell
*Assistant Examiner*—Esther L. Massung
*Attorney, Agent, or Firm*—Bernard J. Burns; George W. F. Simmons; William E. Lambert, III

[57] ABSTRACT

This invention provides a process for preparing a diastase composition as a free-flowing stable powder for use as a source of excess α-amylase to add to flour used for baking purposes.

10 Claims, No Drawings

FREE-FLOWING ENZYME COMPOSITION

This invention relates to $\alpha$-amylase enzyme compositions and to an improved method for preparing them as a free-flowing powder sufficiently stable for commercial use.

Baking and related industries currently increase the naturally occurring diastase in wheat and wheat flour by the addition of a diastase during processing. A minimum level of diastase is necessary to promote adequate gas production and proper starch modification during fermentation of the dough. $\alpha$-Amylase may be added to baking flours in the form of dry powders or in tablets. In either form, it is very important that the enzyme preparation have a highly stabilized diastatic activity.

Fungal diastases are available commercially, for example as Rhozyme diastases which are manufactured by Rohm and Haas Company. Similar diastase preparations may be made in accordance with methods described in the art, as for instance, in U.S. Pat. No. 2,599,532. Under use conditions, the diastatic activity for these preparations is often standardized at 5,000 SKB units per gram of material. This unit expresses the $\alpha$-amylase activity as measured by the method of Sandstedt, Kneen and Blish as described in Cereal Chemistry 16, 712 (1939) "A Standardized Wohlgemuth Procedure for $\alpha$-Amylase Activity."

By diastatic enzyme or diastase there is meant the glycogenic principle which hydrolyzes starch to dextrins and ultimately to glucose and which contains principally $\alpha$-amylases, but there may also be present other enzymic complexes such as esterases, carbohydrases, maltases, peptidases, cellulases, pectinases, and proteases. Further description of such enzyme complexes may be found in the literature such as "The Enzyme" edited by Sumner and Myrback, Academic Press Inc., New York (1952) and "Dynamic Aspects of Biochemistry," E. Baldwin, Cambridge University Press (1952). The enzyme referred to in this invention will most often be referred to as $\alpha$-amylase, but is intended to include all such preparations having this as the major component no matter how made.

The need for adding additional $\alpha$-amylase to flour used for baking purposes manifested itself at the time when combines for harvesting wheat came into general use. Prior to this, wheat was harvested by cutting, forming it into bundles and placing a number of these into a shock. The harvested wheat was then allowed to mature in the shock before it was threshed. During this aging period some of the grain sprouted and this resulted in an increased amounts of active $\alpha$-amylase which ended up in the flour. With the advent of the combine, which combined the harvesting and threshing processes into one, the grain had no opportunity to sprout and thus the milled flour contained but a limited, small quantity of $\alpha$-amylase. A classic source of $\alpha$-amylase was barley malt. However, the amount of diastase in barley malt was uncontrolled and excess proteases were present which hydrolyzed the gluten and caused poor rising of the dough due to an excess loss of gases. A uniform source of $\alpha$-amylase was therefore needed. This invention provides a method for preparing such a product economically.

Heretofore, such compositions have been made by blending a concentrated bacterial or fungal diastatic preparation with an inert filler such as sugars, diatomaceous earth, starch, pectinous materials, dextrins, kaolin and various salts. In these instances, however, the excess water is removed by a prolonged drying process, such as under vacuum, which increases the incidence of decreased diastatic activity due to instability of the diastase under the drying conditions.

The main object of the present invention was to prepare a free-flowing enzyme preparation which was suitable for use in the baking industry from a diastase concentrate which would contain at least 1,000 SKB units, preferably 5,000 SKB units, and which would be stable for at least a 3-month period.

A bacterial or fungal diastase concentrate is a standard preparation well known in the industry and is obtainable by several methods. One common procedure is to grow the culture by a submerged method of preparation or by a tray process, extract the diastase and then to concentrate it by vacuum concentration, reverse osmosis or ultrafiltration. Standard methods employed for the incubation of Aspergilli and for recovering the enzymes from their culture are reviewed in U.S. Pat. No. 3,293,142. Any such concentrate having an SKB value of at least 12,500 units per gram may be used.

Attempts have been made to produce a free-flowing enzyme preparation by adding non-toxic salts capable of forming hydrates such as sodium sulfate, calcium chloride or calcium lactate. The resulting products, however, were not sufficiently stable.

Attempts were also made to make a free-flowing enzyme composition by blending a fungal diastase concentrate with commercial starch which normally contains between 10 and 14% moisture. The resulting products which were produced and which contain the desired diastatic activity as measured by SKB units had more than 8.5% water and had poor storage stability. This instability may in part be due to activity of the proteases present.

For the most part research with the $\alpha$-amylases on starch has been concerned with their purification via their adsorption.

The criterion for storage stability was that it should preferably not lose more than 5% of its diastatic activity per month when stored at 30° C. over an extended period. It was found that this could be achieved for the product herein desired only if the water content was less than 8.5% i.e. a maximum of 8.4%. This was achieved by using low moisture content starch. By this is meant an edible starch suitable for use in the baking industry which has been redried to a maximum moisture content of 3%. Such a redried starch is commercially available.

The general procedure which has been found to give a satisfactory product is to blend an $\alpha$-amylase concentrate having a known water content and SKB units with a sufficient amount of an edible starch having a maximum of 3% water in a proportion such that there is a minimum of 1000 SKB units per gram and a maximum of 8.4% water. Such a product will be free flowing, will have acceptable storage stability and can be used by the baking industry in an amount which is reasonable for augmenting the $\alpha$-amylase content of the floor being employed. For example a reasonable amount is the addition of 5g. of the diastase-starch preparation containing 1000 SKB units per gram to 100 pounds of flour.

The $\alpha$-amylase concentrate which is useful for the purpose is available as liquid food-grade enzyme preparations having a minimum $\alpha$-amylase activity of 12,500

SKB units and is usually between 25 and 30% solids with the remainder as water and a maximum α-amylase activity of about 50,000 SKB units which is usually between 30 and 35% solids and the remainder water. Rhozyme 87-L Concentrate conforms to this range of activity and was convenient for the research herein exemplified.

The edible starch useful for the purpose of this invention may be derived from such diverse sources as banana, bean, cassava, corn, maize, oats, peas, potato, rice and sweet potato. The preferred redried starch is that from corn.

The following examples will illustrate successful preparations which achieved the major object of the invention. These examples are not to be considered in any way as limitations of the scope of this invention and are provided merely as a guide to enable one skilled in the art to better understand the operation of this invention.

EXAMPLE I

One part of Rhozme 87-L Concentrate, a fungal diastase, was mixed with two parts of redried cornstarch (specification — 2% water) and spread out in a thin layer and dried at atmospheric pressure at 45° to 50° C. for 22 hours. The dried product was sieved through a 40-mesh screen and the uniform dried powder was analyzed for diastatic SKB activity. The starting liquid concentrate contained 26,700 SKB units per gram. The prepared dried powder had an activity of 11,100 SKB units per gram which was a 94% recovery of the input SKB activity of the Rhozyme 87-L Concentrate used.

EXAMPLE 2

To 26.5g. of low moisture cornstarch (3% water by analysis) was added 3.0 grams of Rhozyme 87-L Concentrate, a liquid fungal diastase, containing 43,500 SKB units per gram. The fungal diastase was dispersed into the starch with a spatula, care being taken to break up the large moist lumps. To this was added 0.25g. of silicon dioxide in the form of an expanded silica and 0.25g. of tricalcium phosphate. After blending, this was a fairly free-flowing powder containing a few small lumps. The blend was ground in a mortar with a pestle after which it was sifted through a 30-and then a 40-mesh sieve. The sifted blend was placed in a container and tumbled for 15 minutes to insure uniform enzyme dispersion. A free-flowing, lump-free, uniform powder resulted. By analysis, this was found to contain 8.1% moisture. The blend was stored at 30° C. for 110 days with the following results.

| Time (Days) | SKB Units per gram | % Retention |
| --- | --- | --- |
| 0 | 4390 | (110) |
| 30 | 3820 | 87.1 |
| 60 | 3860 | 87.9 |
| 90 | 3846 | 87.6 |
| 110 | 3820 | 87.1 |

The stability of this preparation was considered excellent.

EXAMPLE 3

The procedure of Example 2 as repeated using 27.7g. of the low moisture corn starch and 1.75g. of the Rhozyme 87-L Concentrate. The final blended free-flowing composition contained 7.07% moisture and 2569 SKB units per gram. It was stored at 30° C. for 210 days and the following observations were made.

| Time (Days) | SKB Units per gram | % Retention |
| --- | --- | --- |
| 0 | 2569 | (100) |
| 35 | 2530 | 98.5 |
| 91 | 2000 | 77.9 |
| 146 | 1700 | 67.0 |
| 210 | 1730 | 67.3 |

EXAMPLE 4

The procedure of Example 3 was repeated using the same quantities of corn starch and diastase. The resulting free-flowing powder of uniform particle size contained 6.6% moisture. It was stored as for Example 2 with the following results.

| Time (Days) | SKB Units per gram | % Retention |
| --- | --- | --- |
| 0 | 2430 | (100) |
| 35 | 2310 | 95.2 |
| 91 | 1830 | 75.3 |
| 140 | 1630 | 67.1 |
| 210 | 1668 | 68.6 |

EXAMPLE 5

A blend was made of 25.2g. of redried corn starch containing 3% moisture and 1.4g. Rhozyme 33 concentrate containing 45,000 SKB units per gram. To the blend was added and dispersed 2.0 grams Rhozyme 87-L Concentrate containing 30,000 SKB units per gram. To this was added 0.5g. silicon dioxide and 0.9g. tricalcium phosphate as conditioning agents and the mixture was blended with a spatula to give a free-flowing powder. The blend contained 8.4% moisture and was stored at 30° C. for 92 days. The results of the storage are given below:

| Time (Days) | SKB Units per gram | % Retention |
| --- | --- | --- |
| 0 | 3510 | (100) |
| 35 | 3460 | 98.6 |
| 69 | 3440 | 98.2 |
| 92 | 3500 | 99.7 |

It will be seen that there was essentially no loss of activity.

EXAMPLE 6

A pilot plant preparation was made by placing 2560g. of low moisture corn starch (3% moisture), 50g. of silicon dioxide and 90g. of tricalcium phosphate in a Patterson-Kelly Liquid-Solids Twin Shell Blender Model LBS-8 and mixed for 5 minutes. After this 300g. of Rhozyme 87-L Concentrate containing 43,500 SKB units/g. was added to the still tumbling, dry ingredient blend in 1½ minutes. The blender was rotated for an additional 8½ minutes for a total blending time of 15 minutes. The blend obtained was of uniform particle size, free-flowing and lumpless. By analysis it was found to contain 8.0% moisture. The free-flowing powder was stored at 30° C. for 110 days. The following stability data were obtained:

| Time (Days) | SKB Units per gram | % Retention |
|---|---|---|
| 0 | 3700 | (100) |
| 30 | 3180 | 86.1 |
| 60 | 3200 | 86.5 |
| 90 | 3050 | 82.5 |
| 110 | 3180 | 85.9 |

The blends exemplified above were quite satisfactory for use in the baking industry. Similar preparations made from higher water content starch and containing 8.5% or more of water were unstable on storage and lost so much of their SKB units that they could not be used as an auxiliary source of α-amylase for baking purposes.

The conditioning agents such as silicon dioxide and tricalcium phosphate used in the above examples are not critical with respect to making an α-amylase preparation useful for the baking industry. It is often convenient, however, to add such conditioning agents as an aid in preventing caking and in contributing to the free-flowing properties.

We claim:

1. A process for preparing a stabilized fungal α-amylase composition suitable for use in the baking industry, which comprises uniformly blending a liquid fungal α-amylase concentrate having a minimum diastatic activity of 12,500 SKB units with a sufficient amount of a dried starch containing a maximum of 3% moisture to obtain a free-flowing fungal α-amylase composition having a diastatic activity of at least 1,000 SKB units/gram thereby obtaining maximum water content of 8.4%.

2. A process according to claim 1 wherein the prepared dry fungal α-amylase composition has a diastatic activity of 5,000 SKB units/gram.

3. A process according to claim 1 wherein the dried starch is corn starch.

4. A process according to claim 2 wherein the dried starch is corn starch.

5. A process according to claim 1 which includes the addition of conditioning agents.

6. The stabilized fungal α-amylase composition suitable for the baking industry prepared according to the process of claim 1.

7. A composition according to claim 6 wherein the diastatic activity is 5,000 SKB units/gram.

8. A composition according to claim 6 wherein the redried starch is corn starch.

9. A composition according to claim 7 wherein the redried starch is corn starch.

10. A composition according to claim 6 which includes the addition of the conditioning agents silicon dioxide and tricalcium phosphate.

* * * * *